US008843192B2

(12) United States Patent
Geppert et al.

(10) Patent No.: US 8,843,192 B2
(45) Date of Patent: Sep. 23, 2014

(54) BREAST COIL ARRANGEMENT FOR MAGNETIC RESONANCE APPLICATIONS

(75) Inventors: Christian Geppert, Erlangen (DE); Rainer Kurth, Erlangen (DE); Titus Lanz, Wuerzburg (DE); Florian Odoj, Veitshoechheim (DE); Silke Quick, Erlangen (DE); Christian Schuster, Fuerth (DE); Alexander Weisser, Rimpar (DE); Tobias Wichmann, Rimpar (DE)

(73) Assignee: Siemens Aktiengesellschaft, Munich (DE)

(*) Notice: Subject to any disclaimer, the term of this patent is extended or adjusted under 35 U.S.C. 154(b) by 529 days.

(21) Appl. No.: 12/558,970

(22) Filed: Sep. 14, 2009

(65) Prior Publication Data

US 2010/0099978 A1  Apr. 22, 2010

(30) Foreign Application Priority Data

Sep. 22, 2008 (DE) .................. 10 2008 048 291

(51) Int. Cl.
*A61B 5/055* (2006.01)
*G01R 33/34* (2006.01)
*G01R 33/3415* (2006.01)
*A61B 5/00* (2006.01)

(52) U.S. Cl.
CPC .... *G01R 33/34046* (2013.01); *G01R 33/34084* (2013.01); *A61B 5/0555* (2013.01); *G01R 33/3415* (2013.01); *A61B 5/7207* (2013.01)
USPC .......................................... 600/422; 324/321

(58) Field of Classification Search
USPC .......... 600/410, 415, 421, 422; 324/300, 318, 324/321
See application file for complete search history.

(56) References Cited

U.S. PATENT DOCUMENTS 5,363,845 A * 11/1994 Chowdhury et al. ......... 600/422
5,534,778 A * 7/1996 Loos et al. .................... 600/422
5,590,655 A   1/1997 Hussman
(Continued)

FOREIGN PATENT DOCUMENTS

DE    2007 006 855 A1    8/2008

OTHER PUBLICATIONS

Obi. "A Novel Radio Frequency Coil Design for Breast Cancer Screening in a Magnetic Resonance Imaging System". MS Thesis, Worchester Polytechnic Institute, Dec. 2003. http://www.wpi.edu/Pubs/ETD/Available/etd-0114104-103813/.*

(Continued)

*Primary Examiner* — Unsu Jung
*Assistant Examiner* — Phong K Huynh
(74) *Attorney, Agent, or Firm* — Schiff Hardin LLP

(57) ABSTRACT

A breast coil arrangement for magnetic resonance applications has a placement web that allows an examination subject to lie with her sternum on the placement web with each breast in a receptacle respectively on opposite sides of the placement web. The breast receptacles have limiting elements whose spacing from one another can be adjusted. Multiple array coils are respectively arranged in the limiting elements and are stationary relative to the limiting elements. Each breast receptacle is surrounded by a volume coil that is stationary relative to the placement web. The volume coils are arranged centrally and orthogonally relative to the array coils and surround the array coils. The volume coils are decoupled from the array coils. A spectroscopy phantom can be arranged in proximity to the placement web.

16 Claims, 9 Drawing Sheets

(56) References Cited

U.S. PATENT DOCUMENTS

| | | |
|---|---|---|
| 7,084,631 B2 | 8/2006 | Qu et al. |
| 7,597,104 B2 * | 10/2009 | Zheng et al. ............... 600/415 |
| 2004/0092826 A1 | 5/2004 | Corbeil et al. |
| 2005/0024054 A1 * | 2/2005 | Rinneberg et al. ............ 324/318 |
| 2005/0228267 A1 * | 10/2005 | Bulkes et al. ............... 600/415 |
| 2005/0245805 A1 | 11/2005 | Hoppel et al. |
| 2006/0267587 A1 | 11/2006 | Iwadate et al. |
| 2007/0250047 A1 | 10/2007 | Harter |
| 2009/0054757 A1 | 2/2009 | Noras |

OTHER PUBLICATIONS

Beasley. "Housing Design for a New RF Breast Coil Concept for Use in MRI Applications". BE Project Report, Worchester Polytechnic Institute, Mar. 2008. http://www.wpi.edu/Pubs/E-project/Available/E-project-031008-125605/.*

Chakraborti et al. "Magnetic Resonance Imaging of Breast Masses: Comparison with Mammography". Ind J Radiol Imag 2005 15:3:381-387.*

* cited by examiner

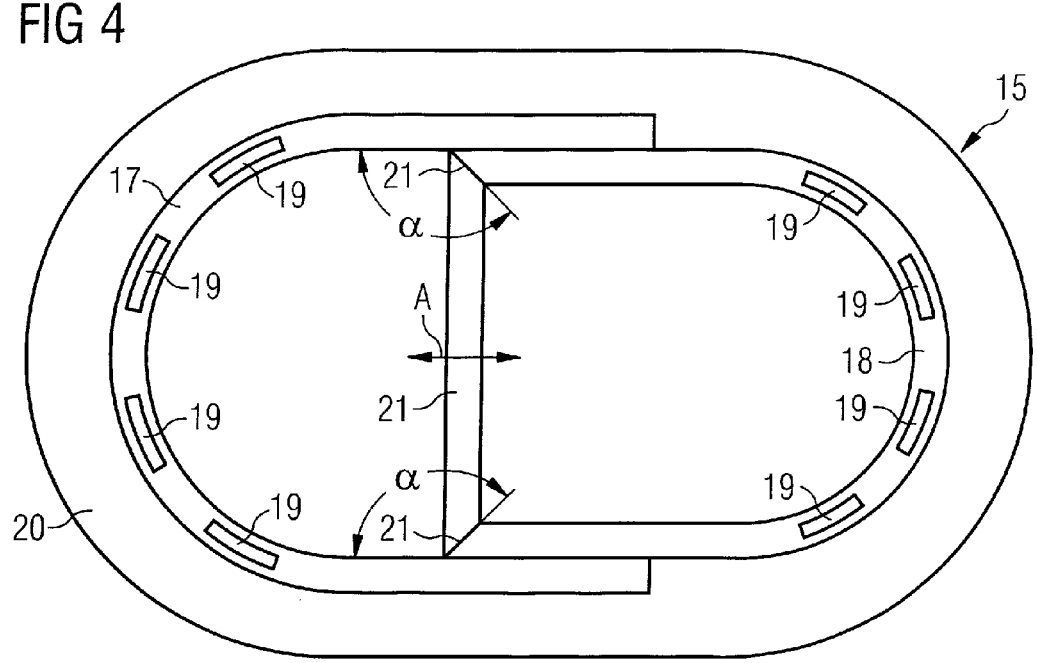
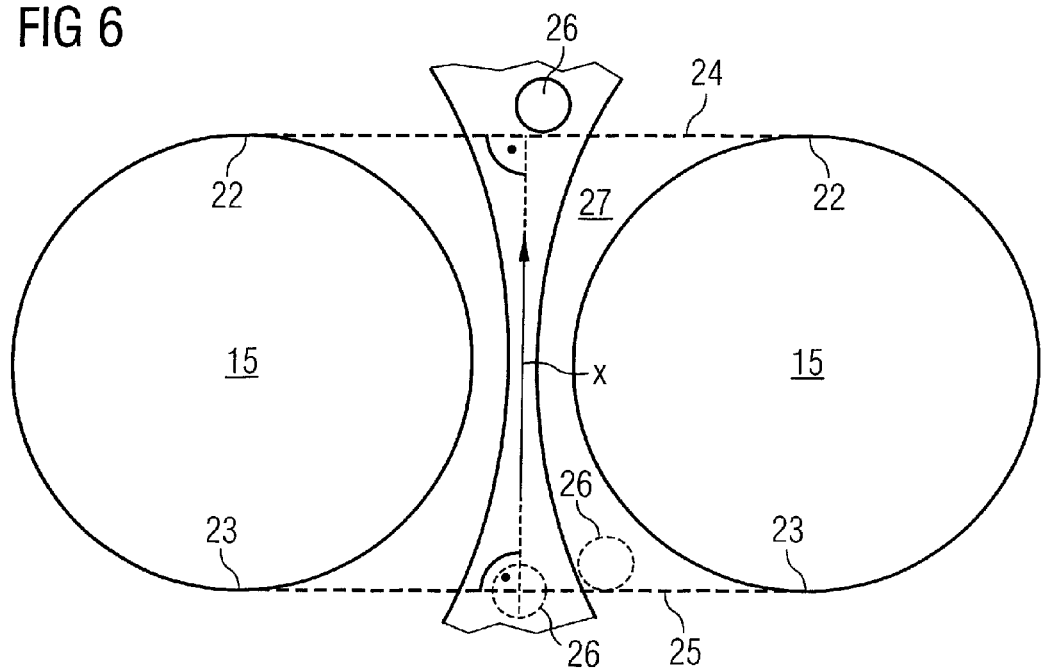

BREAST COIL ARRANGEMENT FOR MAGNETIC RESONANCE APPLICATIONS

BACKGROUND OF THE INVENTION

1. Field of the Invention

The present invention concerns a breast coil arrangement for magnetic resonance applications, of the type having a placement web that is designed so that an examination subject lays with her sternum on the placement web, and a pot-like breast receptacle for each breast of the examination subject on both sides of the placement web.

2. Description of the Prior Art

Breast coil arrangements of the above general type are known in varying designs. For example, a breast coil arrangement of the aforementioned type is known in which every breast receptacle possesses an inner limiting element facing toward the placement web and an outer limiting element facing away from the placement web. The distances of the inner and outer limiting elements from one another can be set so that the size of the respective breast receptacle can be adapted to the size of the breasts of the examination subject. In each of the inner and outer limiting elements, respective multiple array coils are arranged to each detect a magnetic resonance signal, such that the array coils are arranged stationary relative to the respective limiting elements.

Furthermore, a breast coil arrangement of the aforementioned type is known which corresponds in terms of approach to the embodiment that was just described. However, instead of the array coils, each breast receptacle is surrounded by a respective volume coil arranged stationary relative to the placement web.

In both known breast coil arrangements, the inner limiting elements are arranged stationary relative to the placement web. The outer limiting elements are movable.

SUMMARY OF THE INVENTION

An object of the present invention is to provide an improved breast coil arrangement for magnetic resonance applications.

This object is achieved in accordance with the invention by a breast coil arrangement for magnetic resonance applications having a placement web that is designed to allow an examination subject to lie with her sternum on the placement web. Pot-like breast receptacles for each breast of the examination subject are respectively arranged on opposite sides of the placement web. The breast receptacles have limiting elements whose spacing from one another can be adjusted. Multiple array coils are respectively arranged in the limiting elements and are stationary relative to the limiting elements. Each breast receptacle is surrounded by a volume coil that is stationary relative to the placement web. The volume coils are arranged centrally and orthogonally relative to the array coils and surround them. The volume coils are decoupled from the array coils. A spectroscopy phantom can be arranged in proximity to the placement web. The breast receptacles as a structural unit can be detached individually or together from the placement web, and volume-reducing inserts can be inserted into the breast receptacles. Lateral supplementary placement elements carrying axilla coils can be provided and may be separately deactivated depending on an input option of a user.

The invention is based on the two known embodiments described in the preceding are combined with one another. Both the array coils and the volume coils are thus present. The volume coils are hereby arranged centrally and orthogonally relative to the array coils respectively surrounded by them such that—due to the geometric arrangement of the volume coils and the array coils that they respectively surround—the volume coils are decoupled from the array coils that they respectively surround, independent of the adjustment of the respective breast receptacle.

A good signal-to-noise ratio (SNR) results with little effort due to the embodiment according to the invention. In particular, a greater fill factor of the array coils always results due to the ability to place the array coils on the breasts of the examination subject.

In a preferred embodiment, the inner and the outer limiting elements of each breast receptacle adjoin one another at transition regions independent of the setting of the respective breast receptacle and hereby always form obtuse angles with one another at the transition regions. This embodiment allows the breasts of the examination subject are displaced upon adjustment of the breast receptacles but are not pinched.

In an embodiment, the breast coil arrangement has a placement web that is designed so that an examination subject lies with her sternum on the placement web. The breast coil possesses a respective pot-like breast receptacle for each breast of the examination subject on both sides of the placement web. Multiple coils serving for the acquisition of magnetic resonance signals are respectively associated with each breast receptacle. For example, the associated coils can be the array coils and/or the volume coils of the aforementioned embodiment. The remainder of the aforementioned features can also be realized, but this is not absolutely necessary.

Independently of whether the remaining features of the first explained embodiment are realized or not, the breast receptacles are arranged symmetrically relative to the receptacle web. Each breast receptacle has an upper and a lower opening as viewed in the direction of a longitudinal extent of the placement web. An upper connection line connecting the two upper openings with one another and a lower connection line connecting the two lower openings with one another run parallel to one another and orthogonal to the longitudinal extent of the placement web. A spectroscopy phantom is arranged in the region of one of the connection lines and in proximity to the placement web. It is hereby preferable that the spectroscopy phantom is arranged outside of a middle region bounding the two connection lines.

These embodiments allow the spectroscopy phantom to remain in the breast coil arrangement. It does not interfere with the normal operation of the breast coil arrangement. Nevertheless, a spectroscopy and the calibration of the magnetic resonance signal that is connected with this are possible.

In a further embodiment, the breast coil arrangement has a placement web that is designed so that an examination subject lies with her sternum on the placement web. The breast coil has a respective pot-like breast receptacle for each breast of the examination subject on both sides of the placement web. Multiple coils serving to acquire magnetic resonance signals are respectively associated with each breast receptacle. Additional features explained in the preceding in connection with the present invention can also be realized, but this is not absolutely necessary.

According to the invention, the breast receptacles (including the coils associated with them) can as a structural unit be detached individually or together from the placement web without tools. A biopsy coil arrangement as a structural unit can be connected with the placement web without tools as a replacement for the breast receptacles. The biopsy coil arrangement hereby respectively possesses at least one volume coil arranged stationary relative to the placement web for each breast of the examination subject. The breast coil arrangement can be universally used via this embodiment.

The breast coil arrangement in a further embodiment also possesses a placement web that is designed to allow an examination subject to lie with her sternum on the placement web. The breast coil also has respective pot-like breast receptacles for each breast of the examination subject on both sides of the placement web. The additional features of one or more of the preceding embodiments according to the invention can also be realized. Inserts that are stably held in the breast receptacles are inserted into the breast receptacles. Each insert has a curved insert recess on a side facing toward the examination subject, so that the breasts of the examination subject are stably held in the respective insert recesses although the breast receptacles are larger than the breasts of the examination subject. Movement-dependent artifacts can be minimized via this embodiment.

In a preferred embodiment, the inserts respectively border the insert recesses on their sides facing toward the placement web with a respective inner limiting web and respectively border the insert recesses on their sides facing away from the placement web with a respective outer limiting web. For each of the insert recesses, the respective inner limiting web and the respective outer limiting web have differing web thicknesses. This allows the location of the insert recesses to be adapted to the separation between the breasts of the particular examination subject.

Alternatively or additionally each insert my have a curved insert recess on the side facing away from the examination subject so the same inserts (depending on how they are inserted into the breast receptacles) can be used for two breast sizes differing from one another.

The inserts advantageously are formed of a soft material that forms a smooth curve in its region adjoining the breasts of the examination subject. A relatively comfortable body contact with the inserts thereby results for the examination subject.

The above object also is achieved by a breast coil arrangement in accordance with the invention having a placement web that is designed so that an examination subject lies with her sternum on the placement web. The breast coil also has a respective pot-like breast receptacle for each breast of the examination subject on both sides of the placement web. Multiple coils that serve for the acquisition of magnetic resonance signals originating from the region of the respective breast receptacle are respectively associated with each breast receptacle. The breast coil arrangement can be a breast coil arrangement according to any of the embodiments of the present invention that are explained in the preceding. The breast coil arrangement furthermore has supplemental placement elements that, together with the placement web, respectively bifurcate one of the breast receptacles. Axilla coils that serve for the acquisition of magnetic resonance signals originating from the axilla region of the examination subject are integrated into the supplemental placement elements.

The breast coil arrangement according to the invention is used in magnetic resonance systems. In a breast coil arrangement of the type just described it is possible for the coils serving for the acquisition of magnetic resonance signals originating from the region of the respective breast receptacle to be alternatively operated together with the axilla coils, or without the axilla coils, depending on an input option made by a user of the magnetic resonance system. The "normal" coils are thus always operated, but whether the axilla coils are also operated can be chosen by the user.

BRIEF DESCRIPTION OF THE DRAWINGS

FIG. 4 is a section through a breast receptacle along a line IV-IV in FIG. 3.

FIG. 6 is a section through the breast coil arrangement of FIG. 5 along a plane VI in FIG. 5.

DESCRIPTION OF THE PREFERRED EMBODIMENTS

Figure 1:
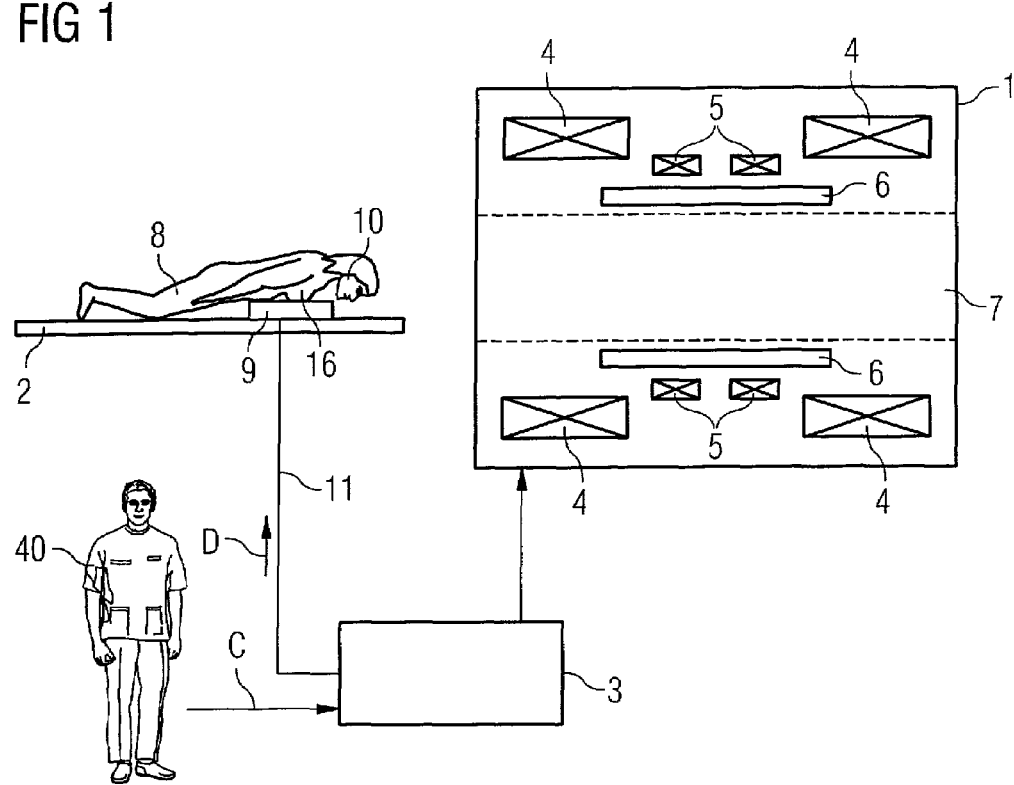
FIG. 1 schematically, a magnetic resonance system, for a breast examination.

As shown in FIG. 1, a magnetic resonance system has a scanner (data acquisition unit) 1, a patient bed 2 and a control device 3. The scanner 1 typically has a basic field magnet system 4, a gradient magnet system 5 and a whole-body coil 6. The basic magnet system 4, the gradient magnet system 5 and the whole-body coil 6 are arranged around a patient tunnel 7. A static, homogeneous basic magnet field is generated in the patient tunnel 7 by the basic field magnet system 4. A gradient field is generated in the patient tunnel 7 by means of the gradient magnet system 5. An examination subject 8 (insofar as she is located in the patient tunnel 7) can be excited to emit magnetic resonance signals by RF radiation from the whole-body coil 6. The gradient magnet system 5 and the whole-body coil 6 are controlled for this purpose by the control device 3.

The examination subject 8 can be driven through the patient tunnel 7 by means of the patient bed 2. Appropriate control of the patient bed 2 by the control device 3 ensues for this purpose. An examination subject 8 would lie with her back on the patient bed 2, but within the scope of the present invention the examination subject 8 (in all cases a woman within the scope of the present invention) lies ventrally on a breast coil arrangement 9. The face 10 of the examination subject 8 thus faces toward the patient bed 2. The breast coil arrangement 9 contains multiple local coils for localized RF transmission/reception. The local coils are not shown in FIG. 1. The local coils are connected with the control device 3 via a shielded multi-core cable 11.

Breast coil arrangements 9 for magnetic resonance applications are generally known. The described embodiments of the breast coil arrangement 9 and its use are the subject matter of the present invention. The present invention is hereby explained in detail in connection with FIGS. 2 through 13.

Figure 2:
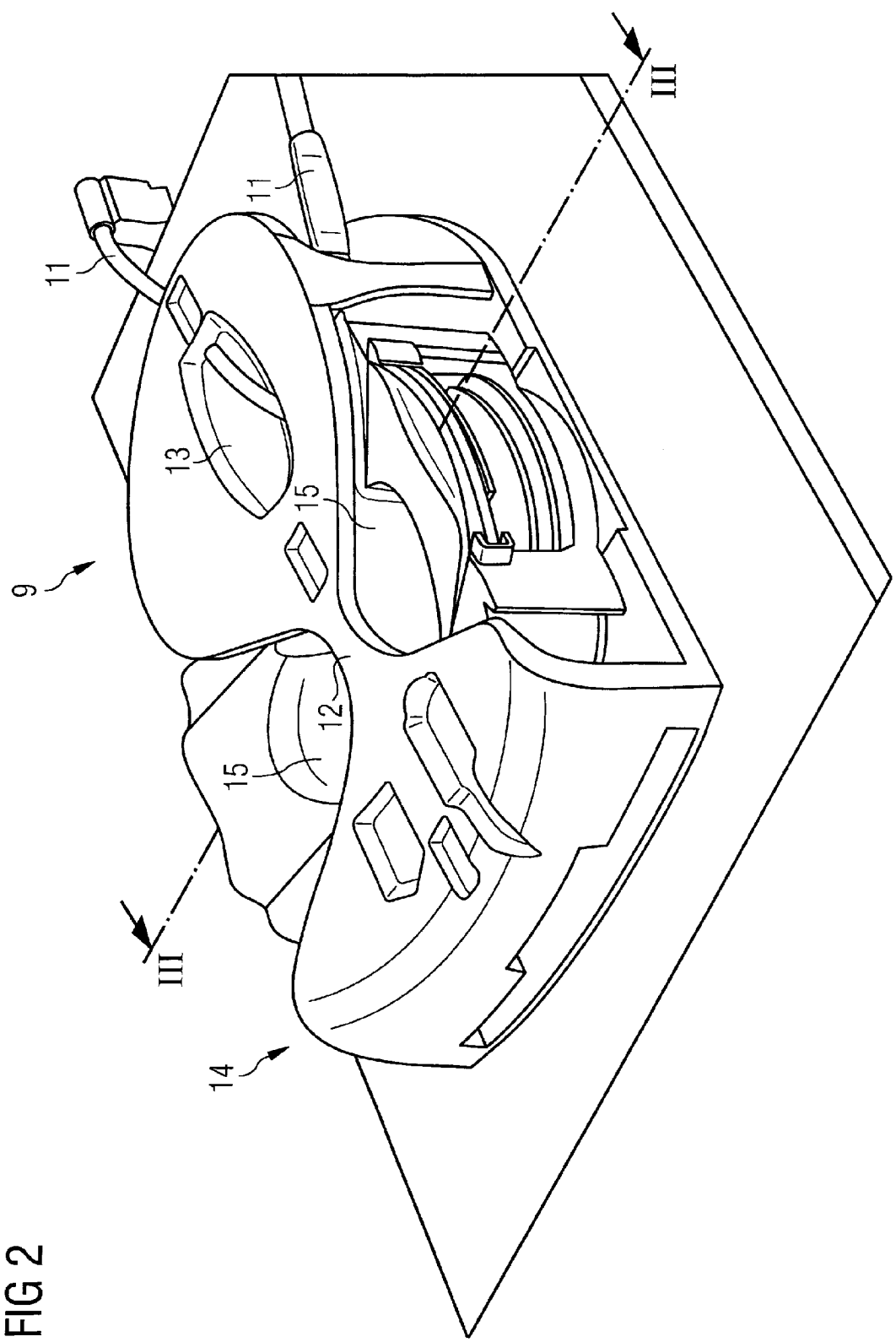
FIG. 2 shows a breast coil arrangement in accordance with the invention.

As shown in FIG. 2, the breast coil arrangement 9 has a placement web 12. The placement web 12 is designed so that the examination subject 8 lies with her sternum on the placement web 12. The face 10 of the examination subject 8 is located in the region of a central opening 13 of the breast coil arrangement 9. Depending on the size of the examination subject 8, the lower ribs of the examination subject 8 are located approximately in the region of the end 14 of the breast coil arrangement 9 that is at a distance from the central opening 13.

On each side of the placement web 12, the breast coil arrangement 9 has one pot-like breast receptacle 15, for each breast 16 (see FIG. 1) of the examination subject 8. Each breast receptacle 15 has an inner limiting element 17 and an outer limiting element 18 (see FIGS. 3 and 4). The L-shape of each inner limiting element 17 faces away from the placement web 12. The L-shape of each outer limiting element 18 faces toward the placement web 12.

The separation (spacing) between each pair of inner and outer limiting elements 17, 18 is adjustable. This is indicated by arrows A in FIGS. 3 and 4. The size of the respective breast receptacle 15 thus can be adapted to the size of the breasts 16 of the examination subject 8.

According to a preferred embodiment, the inner limiting elements 17 are stationary relative to the placement web 12. Only the outer limiting elements 18 are movable. Other embodiments are possible, such as both the inner and the outer limiting elements 17, 18 being adjustable.

Figure 3:
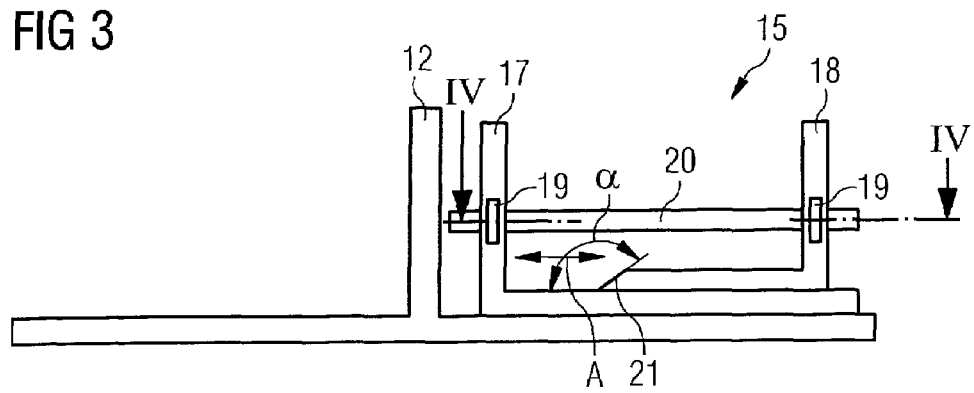
FIG. 3 is a section through the breast coil arrangement of FIG. 2 along line III-III in FIG. 2.

According to FIGS. 3 and 4, multiple array coils 19 are respectively arranged in each of the inner and outer limiting elements 17, 18. The array coils 19 serve to acquire a magnetic resonance signal. The array coils 19 are hereby arranged stationary relative to the respective limiting element 17 or 18. Furthermore, each breast receptacle 15 is surrounded by a respective volume coil 20. The volume coils 20 are stationary relative to the placement web 12. They are thus not moved given an adjustment of the inner and/or outer limiting elements 17, 18. As is particularly clearly visible from FIG. 4, the volume coils 20 are arranged centrally and orthogonally relative to the array coils 19 that they respectively surround. Due to this arrangement, the volume coils 20 are decoupled from the array coils 19 that they respectively surround. Due to the geometric arrangement of the array coils 19 and the volume coils 20, the decoupling is already provided independently of the adjustment of the respective breast receptacle 15, thus independently of the distance of the inner and the outer limiting elements 17, 18 from one another.

According to a preferred embodiment, the inner and the outer limiting elements 17, 18 of each breast receptacle 15 adjoin one another at transition regions 21 independently of the adjustment of the respective breast receptacle 15. Independently of the adjustment of the respective breast receptacle 15, the respective inner and the respective outer limiting elements 17, 18 always exhibit obtuse angles α at the transition regions 21. The angles α can exhibit values differing from one another from transition region 21 to transition region 21, but they are always greater than 90°. Generally they lie in a range from 120 to 150°.

Figure 5:
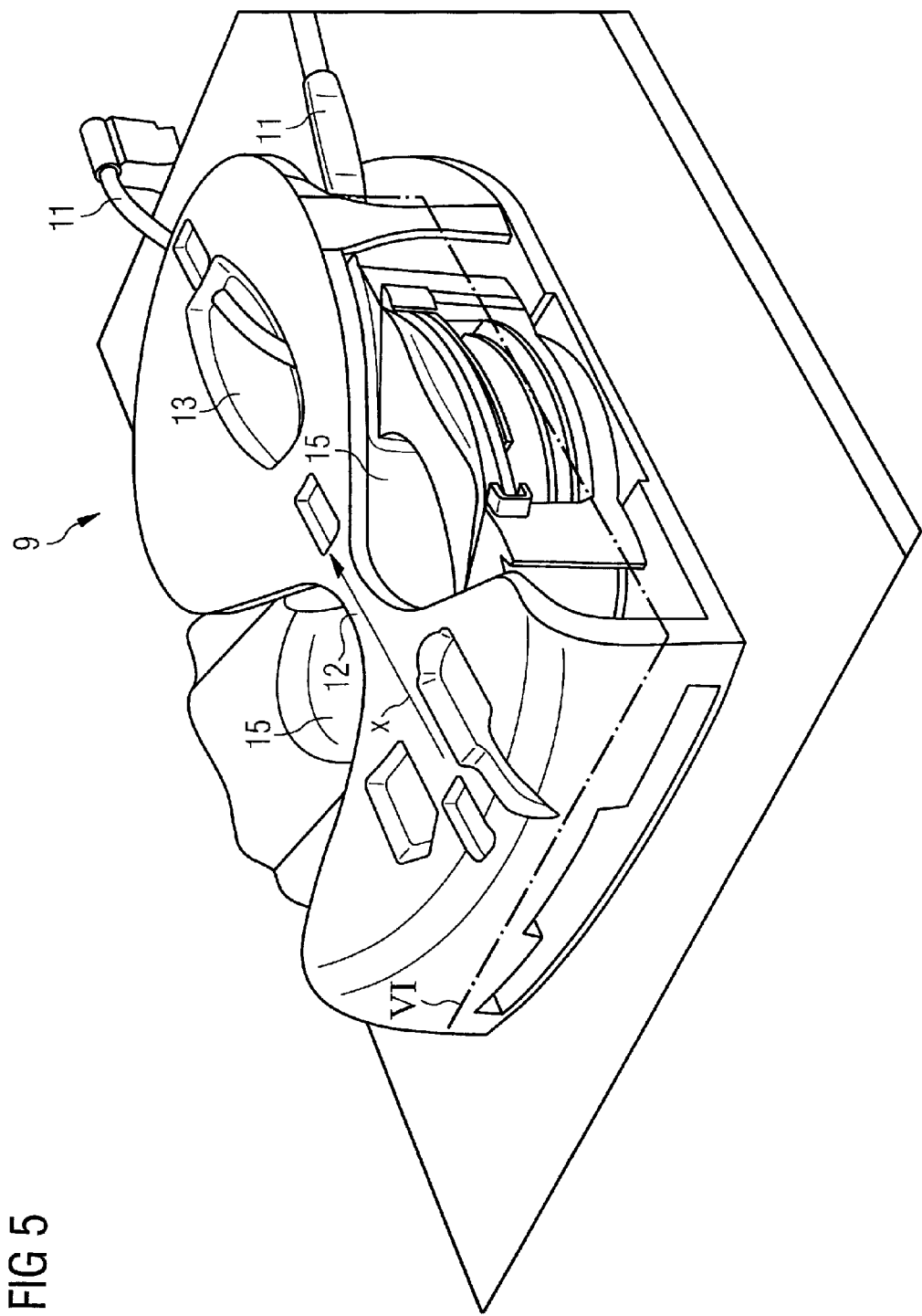
FIG. 5 shows a further embodiment of a breast coil arrangement.

The breast coil arrangement 9 of FIG. 5 also has a placement web 12 that is designed so that the examination subject 8 lies with her sternum on the placement web 12. Furthermore, the breast coil arrangement 9 of FIG. 5 has a pot-like breast receptacle 15 for each breast 16 of the examination subject 8 on each side of the placement web 12. Multiple coils 19, 20 serving for the acquisition of magnetic resonance signals are respectively associated with each breast receptacle 19. The breast coil arrangement 9 according to FIG. 5 can be a breast coil arrangement 9 according to FIGS. 2 through 4. This embodiment is preferred, but is not necessary. Independently of whether the breast coil arrangement 9 of FIG. 5 has the additional features explained in the preceding in connection with FIGS. 2 through 4, the following applies:

The breast receptacles 15 are arranged symmetrically relative to the placement web 12. Each breast receptacle 15 has an upper opening and a lower opening 22, 23 as viewed in the direction of a longitudinal extent x of the placement web 12. Due to this design, an upper connection line 24 which connects the two upper openings 22 with one another runs orthogonally relative to the longitudinal extent x of the placement web 12. A lower connection line 25 which connects the two lower openings 23 with one another likewise runs orthogonal to the longitudinal extent x of the placement web 12. Furthermore, the upper and the lower connection lines 24, 25 proceed parallel to one another.

This embodiment can also be provided in the breast coil arrangement 9 of FIGS. 2 through 4 (at least in the normal case). However, in the breast coil arrangement 9 of FIG. 5, a spectroscopy phantom 26 is arranged in the region of one of the connection lines 24, 25 and in proximity to the placement web 12 (see FIG. 6). In a preferred embodiment (shown in FIG. 6 with solid lines) the spectroscopy phantom 26 is arranged outside of a middle region 27 that is bordered by the two connection lines 24, 25. However, additional possible positionings of the spectroscopy phantom 26 are also drawn with dashed lines in FIG. 6.

Figure 7:
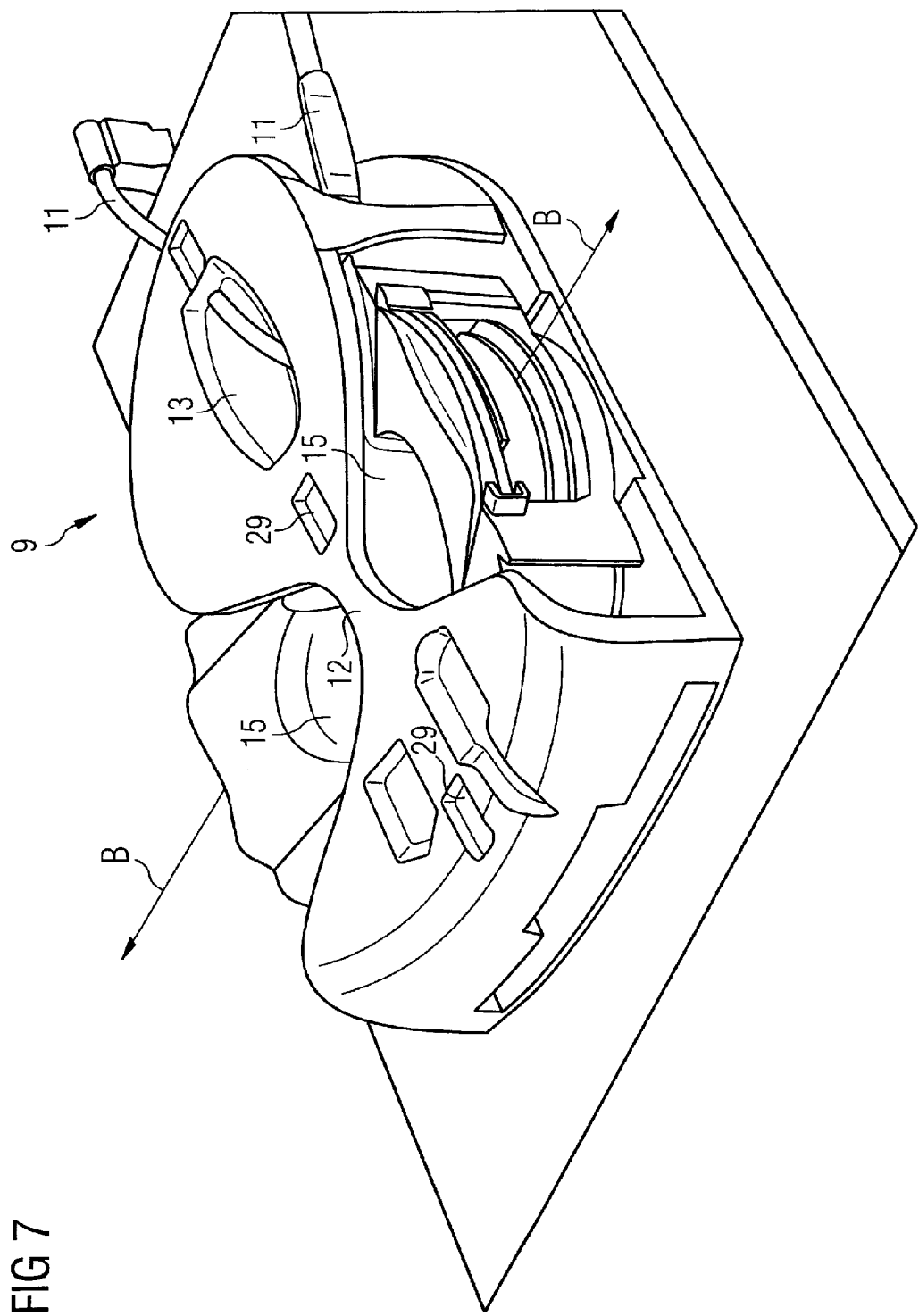
FIG. 7 shows a further embodiment an additional breast coil arrangement of a breast coil arrangement.

The breast coil arrangement 9 according to FIG. 7 also has a placement web 12 that is designed so that the examination subject 8 lies with her sternum on the placement web 12. Furthermore, the breast coil arrangement 9 of FIG. 7 likewise has a pot-like breast receptacle 15 for a breast 16 of the examination subject 8 on each side of the placement web 12. Again, multiple coils 19, 20 serving for the acquisition of magnetic resonance signals are respectively associated with each breast receptacle 15. to this extent the breast coil arrangement 9 of FIG. 7 corresponds with the breast coil arrangement 9 described in the preceding in connection with FIGS. 2 through 4 and FIG. 5. The additional features corresponding to the embodiment of FIGS. 2 through 4 and/or corresponding to the embodiment according to FIGS. 5 and 6 can also be present. This is preferred, but is not necessary.

Independently of whether these additional features are present or not, the breast receptacles 15 are detachable as a structural unit (including the coils 19, 20 associated with them) from the placement web 12. This is indicated by arrows B in FIG. 7. The breast receptacles 15 thus can be detached from the placement web 12 without tools. It can be possible to detach the two breast receptacles 15 from the placement web 12 individually. It is also possible for the two breast receptacles 15 to form a common structural unit.

Figure 8:
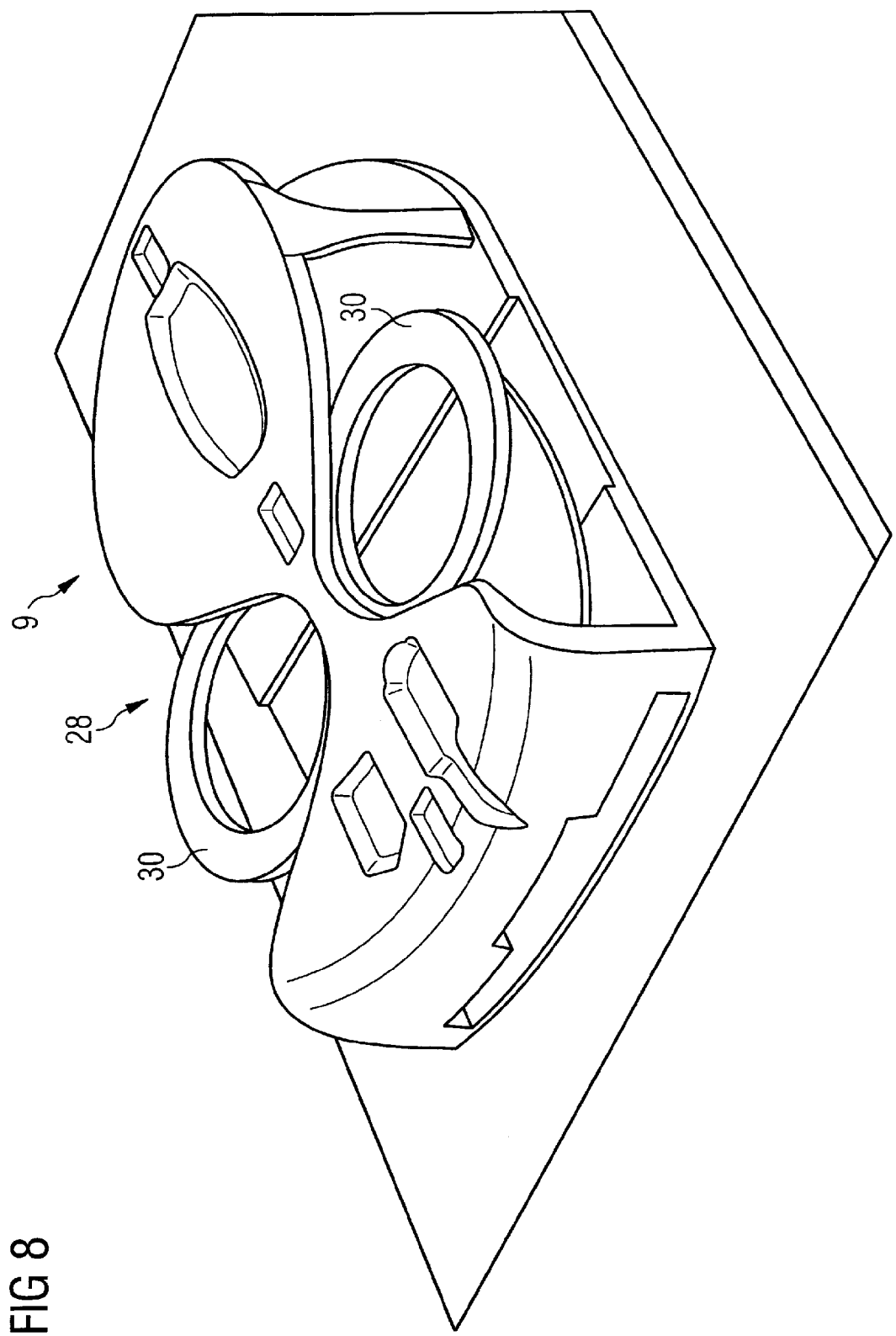
FIG. 8 shows a modification of the breast coil arrangement of FIG. 7.

According to FIG. 8, a biopsy coil arrangement 28 can be connected with the placement web 12 as a replacement for the breast receptacles 15 (likewise as a structural unit and likewise without tools). For example, the preferred embodiment 12 can possess corresponding retention elements 29, for example in the form of hook and loop fasteners (Velcro® tape). The biopsy coil arrangement 28 has at least one volume coil 30 for each breast 16 of the examination subject 8, for example two volume coils 30 per breast 16.

The volume coils 30 are arranged stationary relative to the placement web 12. The breasts 16 of the examination subject 8 are freely accessible to the sides from the outside given use of the biopsy coil arrangement 28, in particular for biopsy purposes.

If the breast coil arrangement 9 of FIG. 7 is fashioned corresponding to FIGS. 2 through 4, the structural unit includes the breast receptacles 15, the limiting elements 17, 18 and the array coils 19 as well as the volume coil 20. If the breast coil arrangement 9 of FIG. 7 is fashioned corresponding to the embodiment of FIGS. 5 and 6, the structural unit advantageously also include the spectroscopy phantom 26. In the individual case, however, the spectroscopy phantom 26 can remain in the breast coil arrangement 9.

Figure 9:
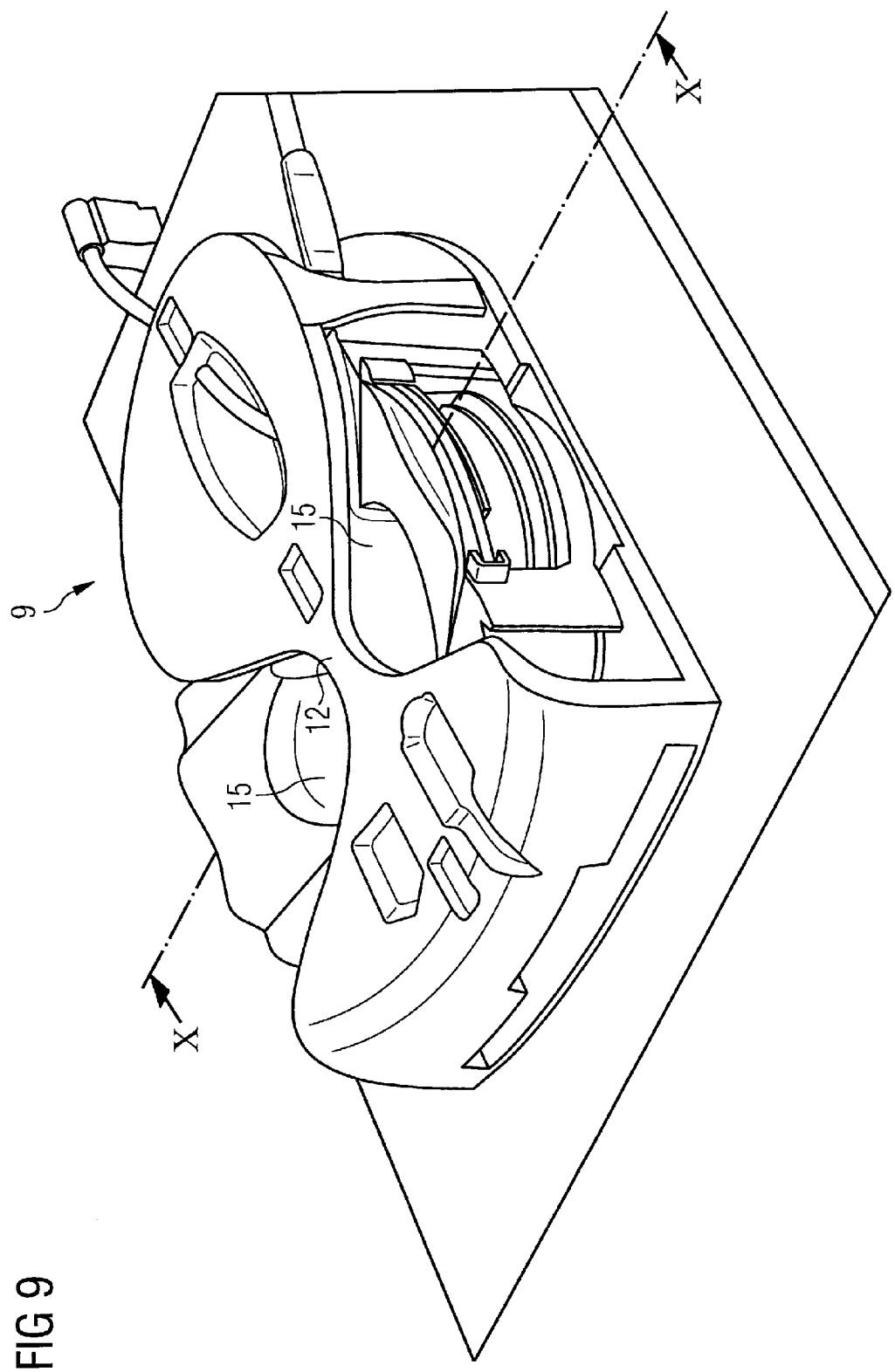
FIG. 9 shows a further embodiment an additional breast coil arrangement of a breast coil arrangement.

The breast coil arrangement 9 according to FIG. 9 also has a placement web 12 that is designed so that the examination subject 8 lies with her sternum on the placement web 12. The breast coil arrangement 9 of FIG. 9 furthermore has a pot-like breast receptacle 15 for each breast 16 of the examination subject 8 on each side of the placement web 12. The additional features of one or more of the embodiments according to FIGS. 2 through 4, 5 and 6 as well as FIGS. 7 and 8 can also be present. This is preferred, but is not necessary. Inserts 31 are inserted into the breast receptacles 15 in the breast coil arrangement 9 according to FIG. 9 (see in particular FIGS. 10 and 11). The inserts 31 are held stably in the breast receptacles 15. On the sides facing toward the examination subject 8, each insert 31 has a curved insert recess 32. Due to the insert recesses 32, the breasts 16 of the examination subject 8 are held stably in the insert recesses 32. This applies although the breast receptacles 15 are larger (in principle or in their current setting) than the breasts 16 of the examination subject 8.

In a preferred embodiment, each insert 31 borders the insert recess 32 with an inner limiting web 33 on the side closer to the placement web 12. Each insert 31 borders the insert recess 32 with an outer limiting web 34 on the side farther away from the placement web 12. The inner limiting web 33 and the outer limiting web 34 respectively exhibit web thicknesses d, d' that differ from one another in each of the insert recesses 32. It is therefore possible to rotate the inserts 31 by 180° around a vertical axis 35 so that the respective inner and outer limiting webs 33, 34 change the position (orientation) of the insert recess 32 relative to the web 12. The location of the insert recesses 32 thus can be adapted to the separation of the breasts 16 of the examination subject 8 from one another via corresponding rotation of the inserts 31 around the respective vertical axes 35.

Figure 10:
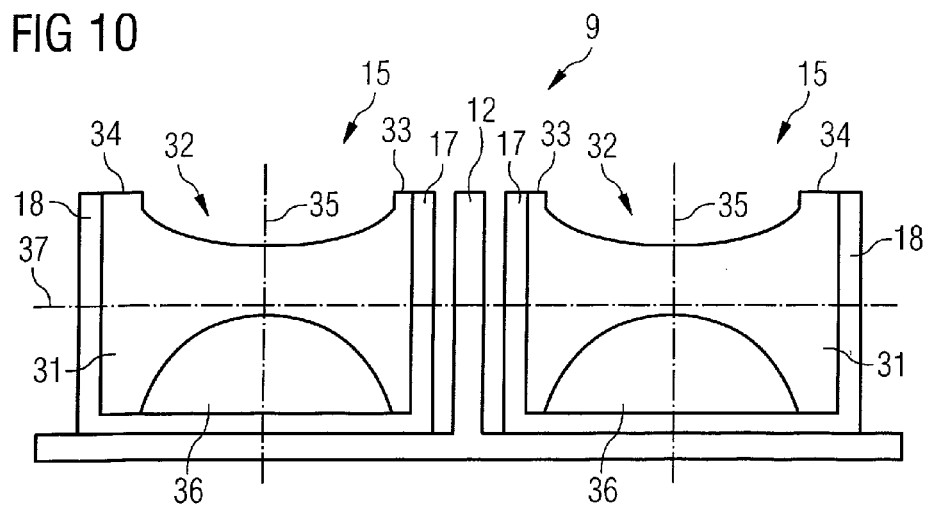
FIG. 10 is a section through a breast receptacle along line X-X in FIG. 9.

As an alternative or in addition to the presence of differing web thicknesses d, d', according to FIG. 10 it is furthermore possible for each insert 31 to have an additional curved insert recess 36 on the side facing away from the examination subject 8. It is therefore possible to rotate the inserts 31 by 180° around a horizontal axis 37 so that the insert recesses 32 and the additional insert recesses 36 exchange their locations. In this way same insert 31 can be used for two different breast sizes of different examination subjects 8.

The inserts 31 advantageously are formed of a soft material (for example a foamed material) so that they are elastically deformable. The material advantageously forms a smooth curve in its region adjoining the breasts 16 of the examination subject 8. A relatively comfortable body contact thereby results for the examination subject 8. In the case of a foamed material, the foamed material is advantageously water-repellent.

The size of the insert recesses 32 and of the additional insert recesses 36 can be selected as needed. A volume ratio of the insert recesses 32 and the additional insert recesses 36 normally is in the range of approximately 2:1.

Figure 12:
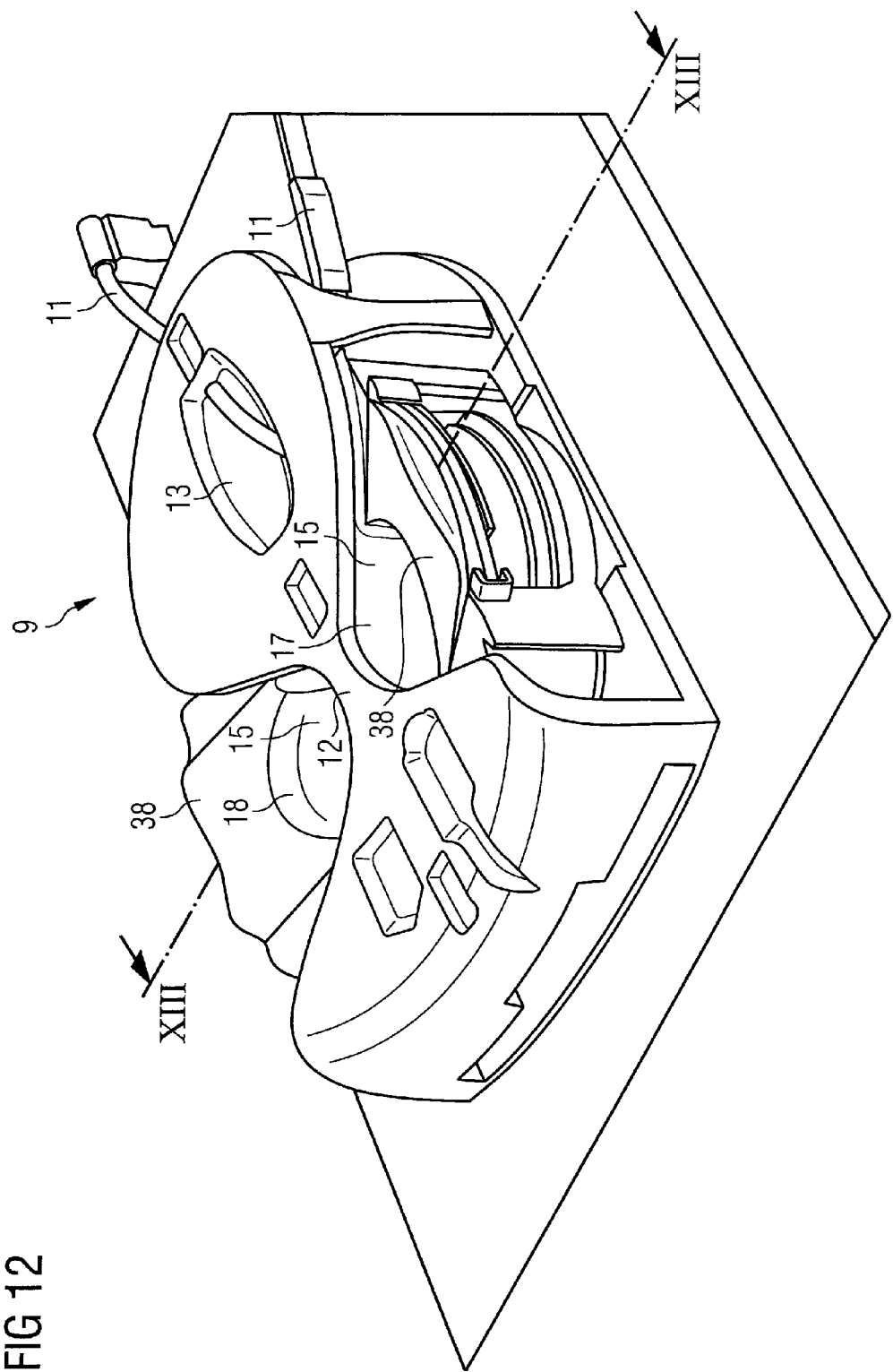
FIG. 12 shows a further embodiment an additional breast coil arrangement of a breast coil arrangement.

In the breast coil arrangement 9 according to FIG. 12, the breast coil arrangement 9 also has a placement web 12 that is designed so that the examination subject 8 lies with her sternum on the placement web 12. Furthermore, in the breast coil arrangement according to FIG. 12 a pot-like breast receptacle 15 is present for each breast 16 of the examination subject 8. Furthermore, multiple coils 19, 20 that serve to acquire magnetic resonance signals originating from the region of the respective breast receptacle 15 are also respectively associated with each breast receptacle 15 in the breast coil arrangement 9 according to FIG. 12.

Figure 11:
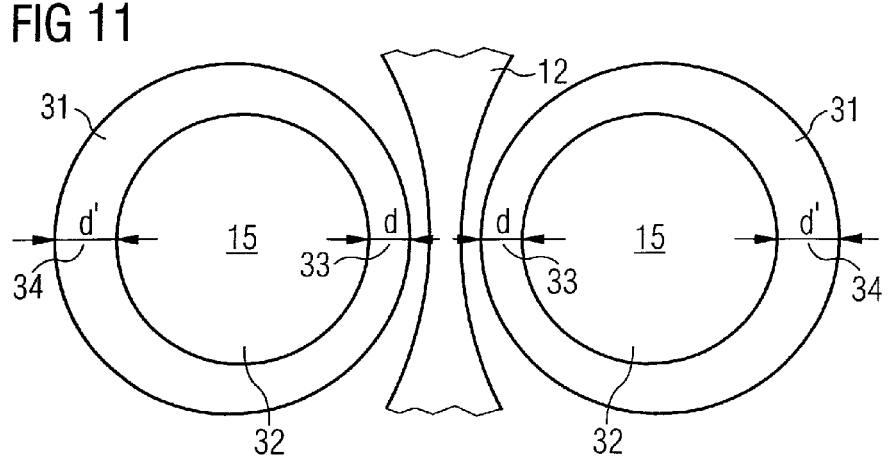
FIG. 11 is a section through a breast receptacle along line XI-XI in FIG. 10.

The breast coil arrangement from FIG. 12 can be a breast coil arrangement 9 according to one or more of the embodiments explained in the preceding, thus according to FIGS. 2 through 4 and/or FIGS. 5 and 6 and/or FIGS. 7 and 8 and/or FIGS. 9 through 11, but this is not necessary.

Figure 13:
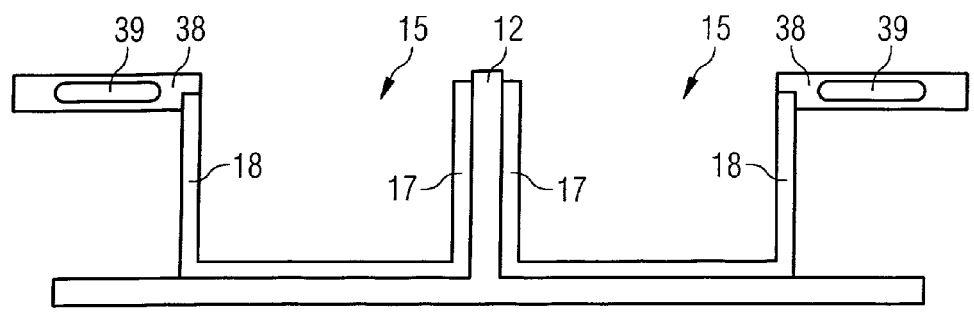
FIG. 13 is a section through the breast coil arrangement of FIG. 12 along line XIII-XIII in FIG. 12.

As shown in FIGS. 12 and 13, the breast coil arrangement 9 has supplementary placement elements 38. The supplementary placement elements 38 together with the placement web 12 respectively bifurcate one of the breast receptacles 15. Axilla coils 39 are integrated into the supplementary placement elements 38. The axilla coils 39 serve for the acquisition of magnetic resonance signals that originate from the axilla region of the examination subject 8.

If the breast coil arrangement 9 according to FIGS. 12 and 13 is fashioned corresponding to FIGS. 2 through 4, the supplementary placement elements 38 are connected with the outer limiting elements 18. If the breast coil arrangement 9 is fashioned corresponding to FIGS. 7 and 8, the supplementary placement elements 38 (and the axilla coils 39) are a component of the removable structural unit.

It is possible to always operate the axilla coils 39 together with the additional coils 19, 20 (thus for example the array coils 19 and the volume coils 20). However, it is advantageously possible for a user 40 of the magnetic resonance system to decide whether to provide a control command C to the control device 3 or not. The control command C represents an input option to the user 40. If the user 40 provides the control command C, the axilla coils 39 are operated. If the user 40 does not provide the control command C, the axilla coils 39 are not operated. In both cases, however, the remaining coils 19, 20 are operated. The selection of the corresponding operating state—operation of the axilla coils 39 or no operation of the axilla coils 39—can be implemented by the control device 3, for example by the control device 3 detuning or not detuning the axilla coils 39 by a corresponding control signal D. The other coils 19, 20 can be operated with a greater sampling at the same resulting spatial resolution due to the deactivation of the axilla coils 39.

Although modifications and changes may be suggested by those skilled in the art, it is the intention of the inventors to embody within the patent warranted hereon all changes and modifications as reasonably and properly come within the scope of their contribution to the art.

We claim as our invention:

1. A breast coil arrangement for magnetic resonance applications, comprising:
   a placement web configured to allow a female examination subject to lie thereon with the sternum on the placement web;
   on each opposite side of said placement web, a pot-like breast receptacle, the respective pot-like breast receptacles being configured to receive the respective breasts of the examination subject therein;
   in each of said breast receptacles, an inner limiting element and an outer limiting element, said inner limiting element being located closer to said placement web than said outer limiting element;
   an adjustment mechanism operable to adjust and set a spacing between said inner and outer limiting elements to adapt respective sizes of the respective breast receptacles to the respective sizes of the breasts of the examination subject;
   in each inner limiting element and outer limiting element in each breast receptacle, multiple array coils configured to at least detect a magnetic resonance signal emitted upon excitation of breast tissue of the breast in the breast receptacle, said array coils being stationary with respect to the respective inner limiting element and outer limiting element in which said array coils are disposed;

for each breast receptacle, a volume coil that surrounds that breast receptacle, each volume coil being stationary relative to said placement web; and for each breast receptacle the volume coil thereof being located centrally and orthogonally relative to the array coils of that breast receptacle and surrounding the array coils of that breast receptacle with said array coils inside said volume coil, and said volume coil and said array coils having a geometrical arrangement with respect to each other configured to decouple the array coils from the volume coil, independently of adjustment of said spacing of the breast receptacle in which the volume coil and the array coils are located.

2. A breast coil arrangement as claimed in claim 1 wherein each inner limiting element is stationary relative to said placement web.

3. A breast coil arrangement as claimed in claim 1 wherein, in each breast receptacle, the inner limiting element and the outer limiting element thereof adjoin each other in a transition region and, independently of adjustment of the size of the breast receptacle, always form an obtuse angle with each other in said transition region.

4. A breast coil arrangement as claimed in claim 1 comprising:
said breast receptacles being located symmetrically relative to said placement web, and each breast receptacle comprising an upper termination and a lower termination along a longitudinal direction of said placement web, with an upper line that is tangential to both breast receptacles and a lower line that is tangential to both breast receptacles proceeding parallel with each other and being orthogonal to said longitudinal direction of said placement web; and a spectroscopy phantom located between said receptacles in proximity to one of said tangential lines and in proximity to said placement web.

5. A breast coil arrangement as claimed in claim 4 wherein said placement web has a central region bordered by said upper and lower tangential lines, and wherein said spectroscopy phantom is located outside of said central region.

6. A breast coil arrangement as claimed in claim 1:
wherein each breast receptacle comprises a first structural unit that mechanically incorporates the coils, the inner and outer limiting elements, and the adjustment mechanism of that receptacle therein, said first structural unit being detachable and removable from the placement web, together with the coils incorporated therein, manually without use of tools;

and wherein said breast coil arrangement comprises a biopsy coil arrangement contained in a second structural unit conforming to said first structural unit and being attachable in place of said first structural unit, manually without tools, to the placement web when said first structural unit is detached and removed from the placement web; and said biopsy coil arrangement comprising at least one volume coil that, when said second structural unit is attached to the placement web, is stationary relative to said placement web.

7. A breast coil as claimed in claim 1 comprising:
in each breast receptacle, an insert that is stably retained in that breast receptacle; and each insert comprising a curved insert recess at a side thereof facing toward the examination subject configured to stably receive and hold a breast of the examination subject therein despite the breast receptacle being larger than the breast of the examination subject.

8. A breast coil arrangement as claimed in claim 7 wherein each insert has an interior in which the breast is located and wherein each insert comprises a circular inner limiting surface and an outer limiting surface surrounding said inner limiting surface, said inner limiting surface having a center that is not centrally located relative to said outer limiting surface, and each receptacle being rotatable around an axis proceeding vertically through said center to selectively position and orient said inner limiting surface relative to the breast in the receptacle.

9. A breast coil arrangement as claimed in claim 7 wherein said curved insert recess is a first curved insert recess, and wherein each insert comprises a second curved insert recess at a side of the insert opposite to said first curved insert recess, said first and second curved insert recesses respectively being curved with different sizes, and each insert being rotatable around an axis proceeding horizontally between said first and second curved recesses to selectively cause one of said first or second curved recesses to face the examination subject, to accommodate different examination subjects with differently sized breasts.

10. A breast coil arrangement as claimed in claim 7 wherein each insert is comprised of material forming a curve that conforms to said curved insert recess.

11. A breast coil arrangement as claimed in claim 1 comprising:
each breast receptacle having a supplemental placement element connected at an exterior thereof at a side of the breast receptacle facing away from the placement web, said supplemental placement element being located along a midline of the breast receptacle that proceeds perpendicularly to said placement web; and each supplemental placement element carrying an axilla coil configured to acquire magnetic resonance signals from tissue in an axilla region of the examination subject.

12. A breast coil arrangement for magnetic resonance applications, comprising:
a placement web configured to allow a female examination subject to lie thereon with the sternum on the placement web;

on each opposite side of said placement web, a pot-like breast receptacle, the respective pot-like breast receptacles being configured to receive the respective breasts of the examination subject therein;

wherein each breast receptacle comprises a first structural unit that mechanically incorporates radio-frequency coils, inner and outer limiting elements that are mechanically adjustable to change a spacing therebetween, and an adjustment mechanism operable to change said spacing, said first structural unit being detachable and removable from the placement web, together with the coils incorporated therein, manually without use of tools;

a biopsy coil arrangement contained in a second structural unit conforming to said first structural unit and being attachable in place of said first structural unit, manually without tools, to the placement web when said first structural unit is detached and removed from the placement web; and said biopsy coil arrangement comprising at least one volume coil that, when said second structural unit is attached to the placement web, is stationary relative to said placement web.

13. A breast coil arrangement for magnetic resonance applications, comprising:
  a placement web configured to allow a female examination subject to lie thereon with the sternum on the placement web;
  on each opposite side of said placement web, a pot-like breast receptacle, the respective pot-like breast receptacles being configured to receive the respective breasts of the examination subject therein;
  in each breast receptacle, an insert that is stably retained in that breast receptacle;
  each insert comprising a curved insert recess at a side thereof facing toward the examination subject configured to stably receive and hold a breast of the examination subject therein despite the breast receptacle being larger than the breast of the examination subject; and
  each insert having an interior in which the breast is located and wherein each insert comprising a circular inner limiting surface and an outer limiting surface surrounding said inner limiting surface, said inner limiting surface having a center that is not centrally located relative to said outer limiting surface, and each receptacle being rotatable around an axis proceeding vertically through said center to selectively position and orient said inner limiting surface relative to the breast in the receptacle.

14. A breast coil arrangement as claimed in claim 13 wherein each insert is comprised of material forming a curve that conforms to said curved insert recess.

15. A breast coil arrangement for magnetic resonance applications, comprising:
  a placement web configured to allow a female examination subject to lie thereon with the sternum on the placement web;
  on each opposite side of said placement web, a pot-like breast receptacle, the respective pot-like breast receptacles being configured to receive the respective breasts of the examination subject therein;
  in each breast receptacle, an insert that is stably retained in that breast receptacle;
  each insert comprising a curved insert recess at a side thereof facing toward the examination subject configured to stably receive and hold a breast of the examination subject therein despite the breast receptacle being larger than the breast of the examination subject; and
  each insert comprising a second curved insert recess at a side of the insert opposite to said first curved insert recess, said first and second curved insert recesses respectively being curved with different sizes, and each insert being rotatable around an axis proceeding horizontally between said first and second curved recesses to selectively cause one of said first or second curved recesses to face the examination subject, to accommodate different examination subjects with differently sized breasts.

16. A breast coil arrangement as claimed in claim 15 wherein each insert is comprised of material forming a curve that conforms to said curved insert recess.

\* \* \* \* \*